United States Patent [19]

Pick

[11] 4,170,300
[45] Oct. 9, 1979

[54] DRESSING CHANGE KITS

[75] Inventor: Ernest W. Pick, Cos Cob, Conn.

[73] Assignee: The Purdue Frederick Company, N.Y.

[21] Appl. No.: 870,590

[22] Filed: Jan. 18, 1978

[51] Int. Cl.² .................. B65D 73/36; B65D 79/00
[52] U.S. Cl. ............................. 206/365; 206/572
[58] Field of Search ................. 128/1 R, 303 R; 206/223, 232, 349, 361–364, 370, 372–373, 438, 440, 499, 560–565, 569–572, 803; 312/209, DIG. 33; 211/60 T

[56] References Cited

U.S. PATENT DOCUMENTS

| | | | |
|---|---|---|---|
| 786,758 | 4/1905 | Gutmann | 206/372 |
| 1,644,830 | 10/1927 | Henderson | 206/572 X |
| 2,135,279 | 11/1938 | Dickinson et al. | 206/571 |
| 3,116,828 | 1/1964 | Glassman | 206/564 |
| 3,396,839 | 8/1968 | Shannon et al. | 206/370 |
| 3,485,352 | 12/1969 | Pilger | 206/365 |
| 3,727,749 | 4/1973 | Martin | 206/560 X |
| 3,987,895 | 10/1976 | Jamshidi | 206/564 X |
| 4,043,754 | 8/1977 | Sklar | 211/60 T X |

Primary Examiner—Davis T. Moorhead
Attorney, Agent, or Firm—Steinberg and Blake

[57] ABSTRACT

A kit for aseptic changing of a dressing such as a catheter dressing includes a disposable tray made of a light plastic sheet material and having a cover sheet adhering thereto and closing depressions in the tray. This cover sheet is removable from the tray so as to render the depressions thereof accessible. In these depressions there are a number of items including packettes of antiseptic germicide solution and ointment, cleansing swabs, and the like, as well as a number of swabsticks, gauze pads, and adherent tape. These items also may include a sheet of drape material, a plastic bag for receiving a previously applied dressing which is removed, and plastic gloves. One of the items included in the tray is a suitable cutting tool, such as a disposable scissors. The tray includes a structure which cooperates with the cutting tool for rendering the latter substantially immovable with respect to the tray so that during transportation and handling of the tray, prior to removable of the cover sheet therefrom, the cutting tool will be incapable of moving about in the tray.

9 Claims, 5 Drawing Figures

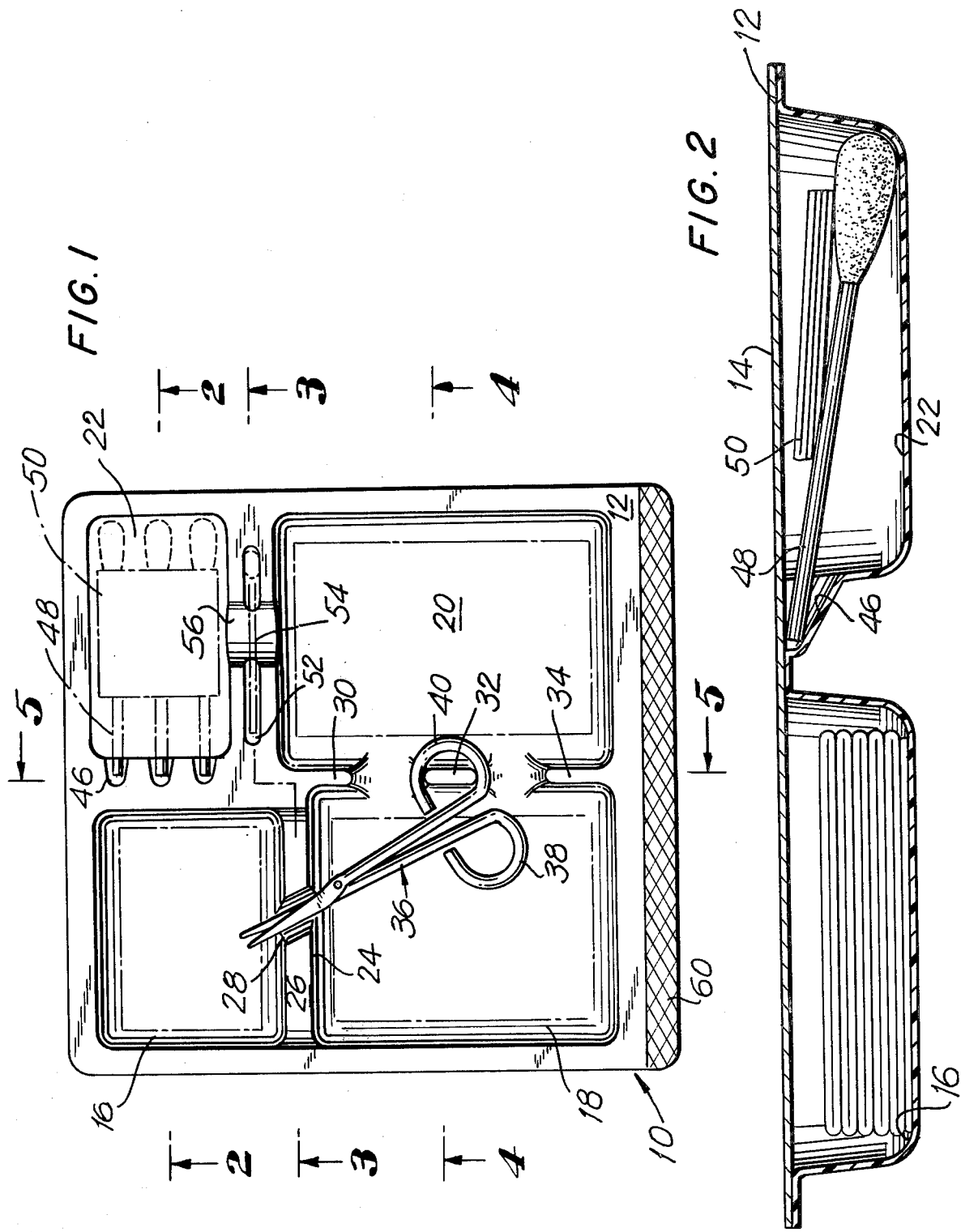

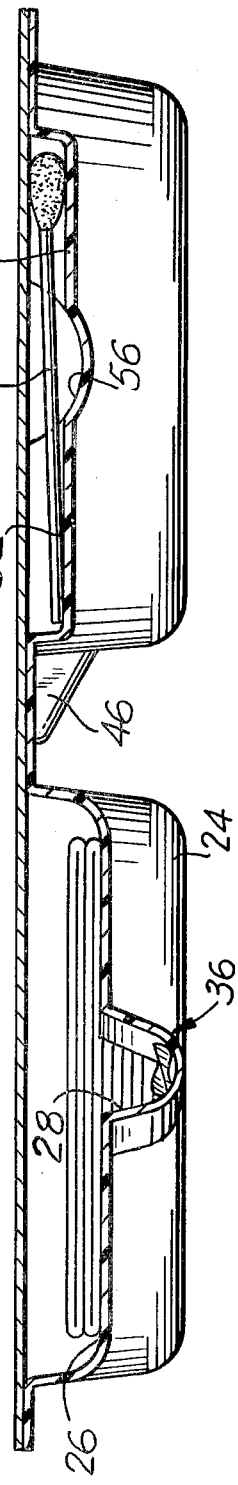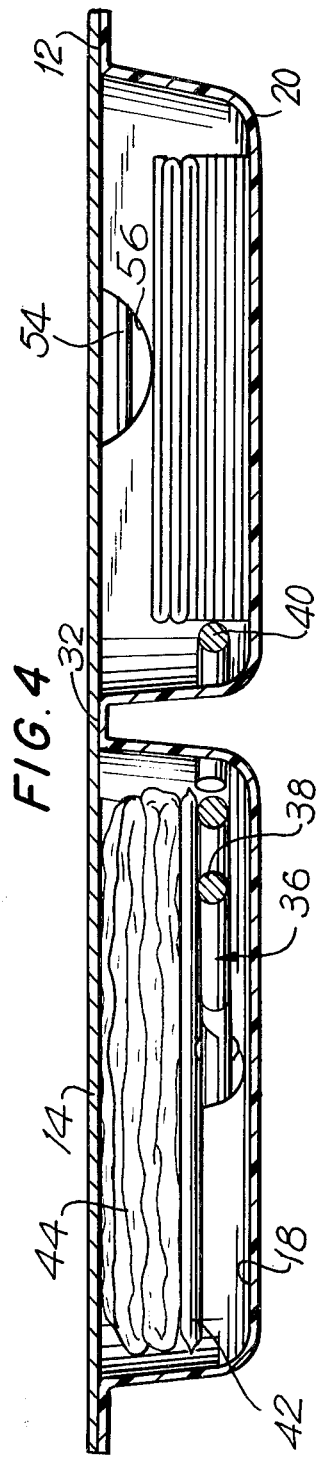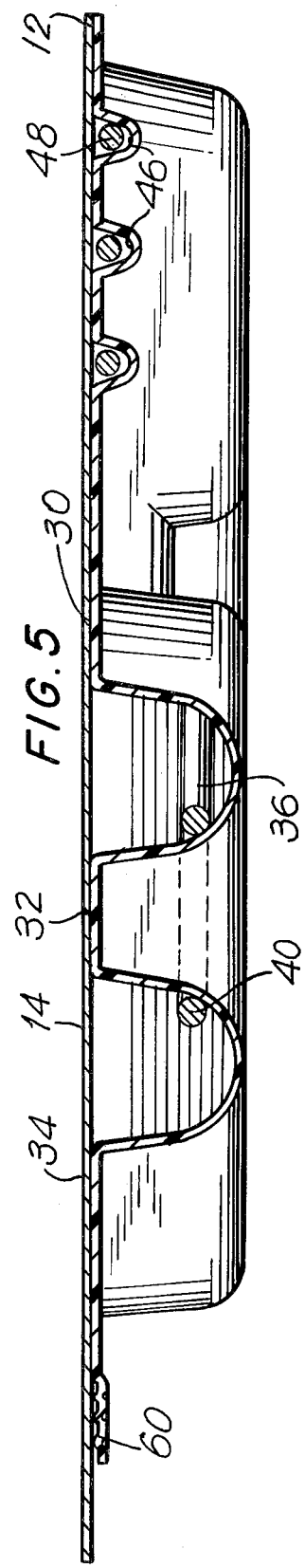

DRESSING CHANGE KITS

BACKGROUND OF THE INVENTION

The present invention relates to dressing change sets or kits enabling dressings, such as catheter dressings, to be changed in an aseptic manner.

It is known to be exceedingly important to carry out dressing change techniques, particularly in connection with catheter care, in an aseptic manner. Experience has shown that almost without exception deviation from such aseptic techniques leads to complications and septicemia.

Problems of this type are particularly encountered in connection with routine dressing changes such as those carried out for changing a central venous catheter dressing, or in connection with the care at the insertion site for any long-line venous catheter including subclavian, jugular, or brachial dressing changes.

A commonly known and rapdily growing long-line procedure is hyperalimentation or total parenteral nutrition. Conditions requiring total parenteral nutrition include carcinoma of the esophogus, carcinoma of the colon, severe peptic ulcer disease with gastric obstruction, prolonged ileus, enterocutaneous fistulae, peritoneal sepsis, biliary or pancreatic fistulae, regional enteritis, transmural and mucosal colitis, diverticulitis, intractable gastroenteritis, hypercatobolic response to major trauma or burns, comatose patients, anorexia nervosa and short bowel syndrome during period of intestinal adaptation.

The average patient placed on total parenteral nutrition remains on it for 20–22 days and requires a dressing change every other day.

Although dressing change sets or kits are already known for the above purposes, the known kits suffer from certain drawbacks. Thus, with conventional sets or kits of the above general type, certain problems are encountered in connection with possible contamination resulting from contact with a previously applied dressing which is removed. Also, previously known kits for the above general purposes do not include the total number of items required for a complete dressing change. Thus, problems are encountered in connection with provision of a suitable container for antiseptic solutions, and in addition to the kits themselves it is necessary to utilize other equipment such as suitable cutting tools required for cutting gauze pads, adherent tapes, and the like. Even if such a kit does include a cutting tool of this type, in the form of a scissors, for example, difficulty is encountered in connection with preventing movement of such a cutting tool with respect to the kit during transportation and handling thereof.

SUMMARY OF THE INVENTION

It is accordingly a primary object of the present invention to provide a kit which will avoid the above drawbacks.

In particular, it is an object of the present invention to provide a kit which on the one hand will include the total of all the items required for bringing about a change of a dressing of the above type and which on the other hand will assure that the technique used in changing the dressing is completely aseptic.

It is a particular object of the present invention to provide a kit of the above type according to which it becomes possible to include in the kit a cutting tool such as a scissors, in such a way that the cutting tool will reliably remain at a predetermined position in the kit during transportation and handling thereof.

Furthermore, it is an object of the present invention to provide a kit of the above type which will also enable items such as swabsticks to be packed in the kit in a manner which will maintain such swabsticks also at a predetermined location in the kit without the possibility of moving about undesirably during transportation of handling of the kit, prior to use thereof in connection with change of a dressing.

In addition, it is an object of the present invention to provide a kit of the above type which is not only fully hygienic in accordance with the highest possible standards of hygiene, but which in addition is relatively inexpensive in its entirety and which is completely disposable.

According to the invention the kit includes a tray which has an upper surface to which a cover sheet adheres in a removable manner, this tray having beneath the cover sheet a number of depressions which are rendered accessible upon removal of the cover sheet. In these depressions there are packed within the tray, beneath the cover sheet thereof, a plurality of items which include, for example, packettes of antiseptic germicide solution and ointment, packettes of cleansing swabs, a number of swabsticks, gauze pads of various sizes, adherent tape, and further items such as a drape, a plastic bag for receiving the removed, previously-applied dressing which is to be discarded, and plastic gloves. In addition, one of the items situated in the tray is a cutting tool such as a disposable scissors. In accordance with a particular feature of the invention the tray includes a means cooperating with the cutting tool to prevent the latter from changing its position in the tray so that during transportation and handling of the tray, prior to removal of the cover sheet therefrom, the cutting tool will not be free to move about in the tray.

BRIEF DESCRIPTION OF DRAWINGS

The invention is illustrated by way of example in the accompanying drawings which form part of this application and in which:

FIG. 1 is a top plan view of a tray of the invention, with the cover sheet removed therefrom so as to illustrate the construction of the tray beneath the cover sheet, with FIG. 1 also showing a scissors situated in the tray, and indicating in phantom lines various items which are also packed in the depressions of the tray; and FIGS. 2-5 are sectional elevations of the tray of FIG. 1 taken respectively along lines 2—2, 3—3, 4—4, and 5—5, of FIG. 1 in the directions of the arrows, indicating not only further details of the tray structure but also showing the cover sheet and indicating schematically various items which are packed in the tray.

DESCRIPTION OF PREFERRED EMBODIMENTS

Referring now to the drawings, there is illustrated therein a tray 10 which forms part of the dressing change kit of the invention. This tray 10 is made of any suitable plastic sheet material. For example the tray 10 may be made of polypropylene, polyethylene, polyvinyl chloride, etc. However, it is preferred to make the tray 10 from a sheet of high-impact styrene which is thermally formed to have the illustrated configuration.

The thin plastic sheet material of the tray 10 is flexible while the tray 10 is capable of having a certain rigidity because of the configuration of the tray 10. Thus the tray 10 includes an upper peripheral wall 12 providing the tray 10 with any upper flat surface area to which it is possible to apply by way of a suitable adhesive a cover sheet 14 indicated in FIGS. 2–5. The cover sheet 14 may simply be made of paper which can easily be peeled away from the upper surface 12 of the tray 10. The upper surface of the cover sheet 14 can have an desired printed matter applied thereto. Also, sheet 14 may be made of spun bond polyolefin.

Beneath the cover sheet 14 the tray 10 includes a number of depressions 16, 18, 20, and 22 all of which are separated from each other by a plurality of partitions which are all hollow and of a substantially U-shaped cross-section, as is apparent from FIGS. 2–5.

The partition 24 which extends between the depressions 16 and 18 has an upper surface 26 which is at an elevation lower than the upper surface 12. This hollow partition 24 is formed between its ends with a transverse inclined notch 28 through which the chambers 16 and 18 communicate with each other. The lower surface of the notch 28 is of the same elevation as the lower surfaces of the depressions 16 and 18.

The partition between the chambers 18 and 20 includes three hollow portions 30, 32, and 34, all of which have upper surfaces at the same elevation as the surface 12 so as to have the cover sheet 14 adhered thereto, as indicated particularly in FIG. 5. The intermediate portion 32 of the partition between the depressions 18 and 20 is separate and spaced from the other portions 30 and 34 of this partition so as to form in this way a hollow upstanding post.

According to a particular feature of the invention, one of the items included in the kit and situated in the tray is a cutting tool 36 in the form of a disposable scissors, as illustrated particularly in FIG. 1. The scissors 36 has a pair of loop-shaped handles 38 and 40 for receiving a thumb and finger of the operator, as is well known. In accordance with the invention the post 32 extends through one of these loops, namely the loop 40 in the example illustrated in FIG. 1. In addition, the length of the scissors 36 is such that a part thereof, namely the blades thereof, extend through the inclined notch 28 of the partition 26 in the manner apparent from FIG. 1. Thus the scissors 36 will at one part of its loop 40 be situated in the chamber 20, while the greatest part of the scissors is situated in the chamber 18. However, the outer tip portions of the blades of the scissors are situated in the chamber 16.

Thus, as a result of this feature of the invention it is possible for the scissors 36 to be maintained in the tray 10 in a predetermined position where the scissors is substantially prevented from moving about with respect to the tray so that an exceedingly convenient kit with respect to transportation and handling thereof, prior to removal of the cover sheet 14, is provided.

A number of additional items are of course also situated within the tray 10. Thus within the depression 18 there are located over the scissors 36 an item such as a relatively large sealed packette 42 (FIG. 4) containing, for example, an antiseptic germicidal solution such as a povidoneiodine solution. Situated above this packette 42 are a pair of plastic gloves 44 which are folded so as to be conveniently situated in the depression 18 over the packette 42 which in turn is over the major part of the scissors 36. Thus, these items 42 and 44 form between the scissors and the cover sheet 14 a cushioning structure which serves to maintain in a yieldable manner the scissors 36 next to the bottom wall of the tray, thus providing in an exceedingly effective packing for the scissors 36 as well as for the items 42 and 44.

The relatively large depression 20 is utilized for accommodating items such as a folded plastic bag which can be used to receive the previously applied dressing which is to be removed and discarded. Also in the depression 20 there is situated a folded drapery sheet, preferably made of a non-woven plastic material. In addition it is possible to situate in the depression 20 a tube of germicidal ointment. This depression 20 also can contain a relatively large rectangular sheet of adherent material having printed thereon certain information such as the date of change, the time, a space for the name of the nurse, etc.

The depression 16 can contain several gauze pads of various sizes, and of course these pads will become situated over the tips of the scissors 36 to become located between these tips and the cover sheet 14, providing a further contribution to the effective packing of the components, including the scissors 36.

It will be seen that because the post 32 is spaced from the partition portions 30 and 34, the depressions 18 and 20 communicate with each other. Also, because of the inclined notch 28 in partition 26 the depressions 16 and 18 communicate with each other. However it will be noted that the depression 22 does not communicate with any of the other depressions. Thus this depression 20 can conveniently serve as a reservoir into which the antiseptic solution from the packette 42 can be poured after the cover sheet 14 is removed and after the packettes is opened.

At the left upper region of the reservoir 22, the tray 10 is formed with a plurality of inclined indentations 46, three such indentations being shown in the illustrated example. These indentations are adapted to receive ends of swabsticks 48 which carry at their right ends, as viewed in FIGS. 1 and 2, cotton wadding or the like. Thus as is particularly apparent from FIG. 2 the swabsticks 48 are packed in the inclined condition illustrated. Situated above the swabsticks in the depression 22 are a plurality of cleansing swabs such as acetone/alcohol swabs, these swabs being situated in suitable packettes 50. Thus with these packettes 50 of the cleansing swabs situated above the sticks 48, between the latter and the cover sheet 14, the swabsticks 48 also will be retained in the position illustrated in FIG. 2 until the cover sheet 14 is removed.

In addition, the wall portion of the partition between the depressions 20 and 22 is formed at its upper surface with a horizontal groove 52 (FIG. 3), and this groove receives a smaller swabstick 54 which may be utilized for spreading the antiseptic ointment. The upper wall portion of the partition between the chambers 20 and 22 is formed with an indentation 56 extending across the groove 52, and it will be seen from FIG. 3 that the stick 54 thus extends freely across the indentation 56, so that the stick 54 is easily accessible and can readily be removed for use.

As a further feature of the invention, one of the items in the chamber 20 may include a folded sheet carrying printed instructions.

As is apparent particularly from FIGS. 1 and 5, the cover sheet 14 extends beyond one edge of the tray 10, and this edge region 60 of the tray 10 is suitably waffled, so as to facilitate grasping and holding of the tray 10 and prevent excessive adherence of the cover sheet 14 thereto. Of course the fact that the sheet 14 extends beyond the waffled edge region 60 enables the cover sheet 14 to be easily grasped and removed from the tray 10.

In order to use the above structure of the invention, in accordance with instructions on the instruction sheet, after the cover sheet 14 is removed, the plastic bag for receiving the previously applied dressing which is to be discarded can be hung at any suitable location and the drapery sheet is placed on the patient adjacent the area where the dressing is to be changed. Of course, after the cover sheet is removed the individual applying the dressing will carefully wash his hands with an antiseptic cleansing solution. The acetone/alcohol swabs are utilized to cleanse the skin around the insertion site of the catheter, with repetition of this cleansing operation being provided as required. Then the operator will again wash the hands and will apply the plastic gloves 34 utilizing an aseptic technique.

At this time the packette 42 of antiseptic germicidal solution will be opened and spilled into the reservoir 22 so that the heads of the swabsticks 48 will be immersed in this solution. Then these swabsticks are used as required for prepping the skin area around the insertion site, with the operator making sure that the catheter itself is covered. Fresh swabsticks 48 are utilized as required.

At this time a germicidal antiseptic ointment may be applied utilizing for this purpose the packette of ointment taken from the depression 20 and the swabstick 54.

Now the scissors 36 are removed and the gauze pads taken from the depression 16 are partially cut through so as to have slits through which the catheter tube can extend while the gauze pads are placed at the insertion site. One of the gauze pads is larger than the others and covers the entire dressing which has been applied up to this point.

Now the operator can remove from the depression 20 the relatively large sheet of adherent tape, to which information can be applied as referred to above, with the scissors again being used to cut an elongated edge region from this tape. The tape is placed over the entire dressing, including the catheter tube which is then looped around an edge of the tape and across the upper surface thereof. Now the relatively thin elongated portion of the adherent tape which has been removed is placed over the tube adhering the latter to the upper surface of the previously applied adherent tape.

These simple operations complete the change of dressing in an entirely aseptic manner. All of the items can be discarded, being placed for this purpose in the plastic bag which received the previously applied dressing which has been removed. A suitable closure is provided for the plastic bag, so that all of the contents placed therein will reliably remain therein upon discarding of the bag with the contents therein.

It is thus apparent that with the kit of the invention, although the structure thereof is exceedingly simple and inexpensive, nevertheless an exceedingly effective dressing change operation can be carried out while assuring the highest standards of aseptic technique, particularly in connection with catheter care, thus avoiding the possibility of any complications and septicemia.

What is claimed is:

1. A kit for aseptic change of a dressing such as a catheter dressing, comprising a tray having an upper surface carrying a cover sheet which adheres to said upper surface while being removable therefrom, said tray being formed with a plurality of depressions which are covered and closed by said cover sheet and which are rendered accessible upon removal of said cover sheet from said tray, a plurality of items in said depressions to be rendered accessible upon removal of said cover sheet from said tray, said items including packettes of cleansing swabs, packettes of antiseptic solution and ointment, swabsticks, gauze pads, adherent tape, as well as further items such as plastic gloves, a plastic bag for receiving a previously applied dressing which is removed, and a drape, and one of said items being a disposable pair of scissors having a pair of loop-shaped handles for receiving a thumb and finger of the operator for cutting items such as one or more gauze pads, adherent tape, or the like, said tray including means defined by said tray including a post which extends through one of said loop-shaped handles of said scissors and a partition separating a pair of depressions from each other, said partition being formed with a notch passing therethrough and receiving a part of said scissors distant from said looped handle portion thereof through which said post extends, for maintaining the latter at a predetermined location in said tray so as substantially to prevent undesired movement of said scissors with respect to said tray during handling and transportation thereof prior to removal of said cover sheet therefrom.

2. The combination of claim 1 and wherein the part of said scissors which extends through said notch of said partition includes blades of said scissors.

3. The combination of claim 2 and wherein a plurality of said items such as said plastic gloves and one or more of said packettes are situated between said cover sheet and scissors for contributing to prevention of movement thereof with respect to said tray during transportation and handling thereof.

4. The combination of claim 3 and wherein said tray is made in its entirety of a relatively thin plastic sheet material with said post and said partition of said tray both being hollow.

5. The combination of claim 4 and wherein one of said depressions of said tray forms a reservoir for receiving antiseptic solution from one of said packettes, and some of said swabsticks being situtated in part in said reservoir while said tray has adjacent said reservoir a plurality of indentations for supporting portions of the latter swabsticks which extend beyond said reservoir.

6. The combination of claim 5 and wherein said tray also is formed at its upper surface region with an elongated groove for accommodating a swabstick, and said tray being formed with an indentation extending across said groove between the ends thereof, so that the swabstick which is situated in said groove extends across the latter indentation to be rendered easily accessible at said latter indentation.

7. The combination of claim 1 and wherein said cover sheet is made of paper.

8. The combination of claim 1 and wherein said items include a sheet of instructions.

9. The combination of claim 1 and wherein said cover sheet is made of spun bond polyolefin.

* * * * *